United States Patent
Wang et al.

(10) Patent No.: US 12,297,518 B2
(45) Date of Patent: May 13, 2025

(54) LITHIUM RECOVERY PROCESS

(71) Applicant: Worcester Polytechnic Institute, Worcester, MA (US)

(72) Inventors: Yan Wang, Acton, MA (US); Jiahui Hou, Worcester, MA (US); Xiaotu Ma, Worcester, MA (US); Jinzhao Fu, Worcester, MA (US)

(73) Assignee: Worcester Polytechnic Institute, Worcester, MA (US)

( * ) Notice: Subject to any disclaimer, the term of this patent is extended or adjusted under 35 U.S.C. 154(b) by 615 days.

(21) Appl. No.: 17/719,080

(22) Filed: Apr. 12, 2022

(65) Prior Publication Data
US 2022/0325378 A1   Oct. 13, 2022

Related U.S. Application Data

(60) Provisional application No. 63/174,068, filed on Apr. 13, 2021.

(51) Int. Cl.
*C22B 26/12* (2006.01)
*A63B 24/00* (2006.01)
(Continued)

(52) U.S. Cl.
CPC .......... *C22B 26/12* (2013.01); *A63B 24/0075* (2013.01); *C01D 15/08* (2013.01);
(Continued)

(58) Field of Classification Search
CPC .......... C22B 26/12; C22B 3/06; G16H 20/30; A63B 24/0075; C01D 15/08; H01M 10/54
See application file for complete search history.

(56) References Cited

U.S. PATENT DOCUMENTS

| 8,741,150 B2 | 6/2014 | Chung et al. |
| 9,972,830 B2 | 5/2018 | Poe et al. |
| 2017/0077564 A1 | 3/2017 | Wang et al. |

FOREIGN PATENT DOCUMENTS

| CN | 108923096 A | 11/2018 |
| CN | 107017443 B | 4/2019 |

(Continued)

OTHER PUBLICATIONS

Gao, Wenfang et al., "Lithium carbonate recovery from cathode scrap of spent lithium-ion battery: a closed-loop process", Environmental Science & Technology, Jan. 12, 2017 (Publication date), vol. 51, pp. 1662-1669.
(Continued)

*Primary Examiner* — Ian A Rummel
*Assistant Examiner* — Annette Phan
(74) *Attorney, Agent, or Firm* — Armis IP Law, LLC

(57) ABSTRACT

Lithium recycling from expended Li-Ion batteries occurs thought selective recovery of lithium charge materials from a recycling stream including transition metals used for the charge material. Li recovery includes dissolving the lithium based charge material in an organic acid having a resistance or lack of affinity to dissolution of transition metals, and distilling a leach solution formed from the dissolved charge material for generating a powder including lithium and trace impurities of the transition metals. Sintering of the generated powder forms lithium carbonate and carbonates of the trace impurities that eluded the selective leach, however, since the trace impurities are insoluble in water, the lithium carbonate is recoverable by water washing.

20 Claims, 15 Drawing Sheets

(51) Int. Cl.
  *C01D 15/08*  (2006.01)
  *C22B 3/06*  (2006.01)
  *G16H 20/30*  (2018.01)
  *H01M 10/54*  (2006.01)

(52) U.S. Cl.
  CPC .............. *C22B 3/06* (2013.01); *G16H 20/30* (2018.01); *H01M 10/54* (2013.01); *A63B 2024/0068* (2013.01); *A63B 2230/60* (2013.01)

(56) References Cited

FOREIGN PATENT DOCUMENTS

| | | |
|---|---|---|
| JP | 4581553 B2 | 11/2010 |
| JP | 4767798 B2 | 9/2011 |
| JP | 2013051119 A | 3/2013 |
| KR | 101036407 B1 | 5/2011 |
| WO | WO-2020011765 A1 * | 1/2020 ............. C22B 1/005 |

OTHER PUBLICATIONS

International Search Report, PCT/US2022/024431, Aug. 5, 2022, pp. 1-3.

\* cited by examiner

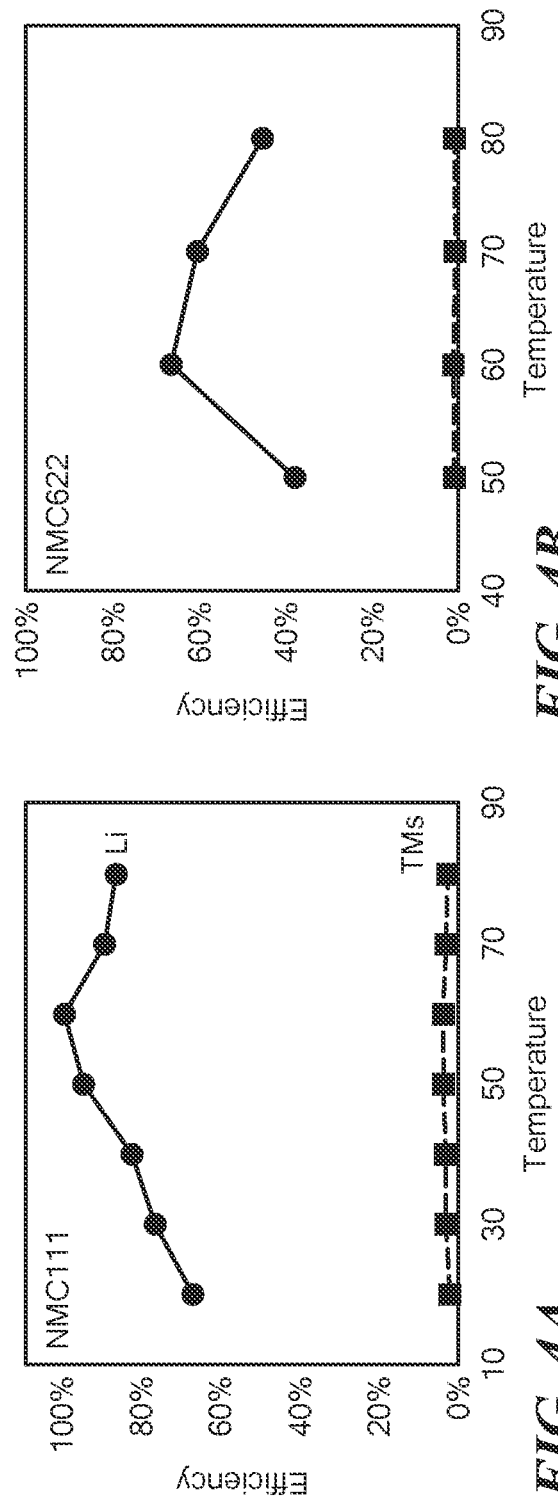
FIG. 4A
FIG. 4B
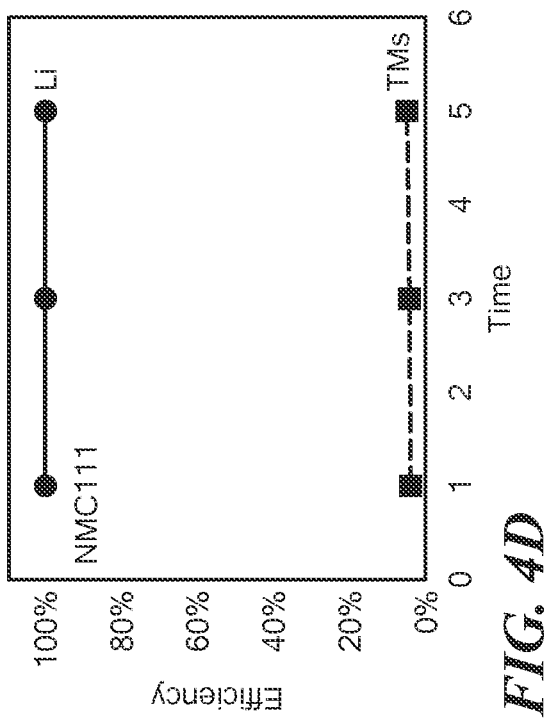
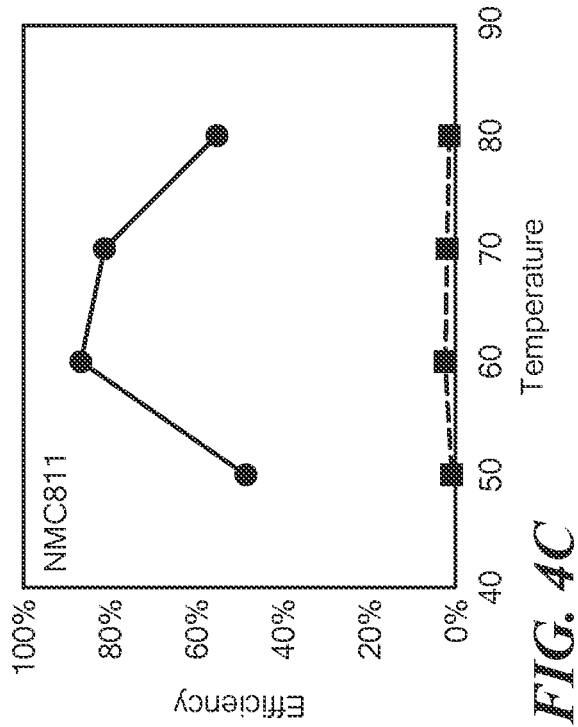
FIG. 4C
FIG. 4D

LITHIUM RECOVERY PROCESS

RELATED APPLICATIONS

This patent application claims the benefit under 35 U.S.C. § 119(e) of U.S. Provisional Patent App. No. 63/174,068, filed Apr. 13, 2021, entitled "LITHIUM RECOVERY PROCESS," incorporated herein by reference in entirety.

BACKGROUND

The wide applications of lithium-ion batteries (LIBs) are directly driven by their excellent performance in power sources, mobile electronics and energy storage devices. Moreover, LIB s dominate the electric vehicle market due to their high energy density. With the increasing demand of electric vehicles (EVs), a corresponding increase in spent LIB battery packs can be expected. Thus, sustainable LIBs systems will become increasingly significant.

Lithium is a primary element in LIB s, which is mainly applied in cathode materials and electrolytes. In 2019, 65% of lithium consumption was for battery applications, a 30% increase from 2015, resulting in the most significant source of lithium consumption. From 2018 to 2019, the consumption of lithium rose 18%, from 49,100 tons to 57,700 tons. If the annual growth rate of lithium demand remains, the global lithium reservoir runs a risk of exhaustion; and it further pushes production in a direction such that the demand may outstrip supply. Financial ramifications can also be expected to follow.

SUMMARY

A closed loop process for lithium recycling for LIBs combines selective leaching of recycling stream charge materials for lithium extraction with sintering and precipitation. An organic acid such as formic acid leaches lithium from cathode materials. Sintering and precipitation further purifies the lithium, which results in a purity above 99% by the disclosed process.

Configurations herein are based, in part, on the observation that secondary (rechargeable) batteries are becoming increasingly utilized for electrical based energy in a wide variety of commercial applications, such as portable devices (i.e. cell phones), battery powered tools and lighting, and more significantly, in EV (electric vehicles) and hybrid vehicles. The widespread use of EVs will generate considerable charge material waste streams amenable to recycling. Unfortunately, conventional recycling processes for battery waste streams often focus on the transition metals (Ni, Mn, Co, Cu and others), rather than the lithium (Li), and tend to operate on pyrometallurgical processes that involve substantial heating, or uses hydrometallurgical processes. For both Pyrometallurgical and hydrometallurgical processes, lithium may not be recycled or recycled at lower efficiency or purity.

Accordingly, configurations herein substantially overcome the shortcomings of low efficiency or purity associated with conventional approaches by specifically targeting lithium in a recycling stream of charge materials, and extracting highly pure lithium by selective leaching of only the lithium using an organic acid such as formic acid. Impurities circumventing the selective leach, typically less than 5% of Ni, Mn, Co, are subsequently removed by forming water insoluble transition metal carbonates and dissolving the lithium carbonate through water washing for subsequent precipitation with acetone.

In further detail, in a battery recycling environment for rechargeable cells, a method for selective recovery of lithium charge materials from a recycling stream including transition metals includes dissolving the lithium based charge material in an organic acid having a resistance or lack of affinity to dissolution of transition metals, and distilling a leach solution formed from the dissolved charge material for generating a powder including lithium and trace impurities of the transition metals. Sintering of the generated powder forms lithium carbonate and carbonates of the trace impurities that eluded the selective leach, however, since the trace impurities are insoluble in water, the lithium carbonate is recoverable by water washing. Then lithium carbonate can be precipitated after the solution is transferred into acetone and pure lithium carbonate can be filtered and collected.

BRIEF DESCRIPTION OF THE DRAWINGS

The foregoing and other objects, features and advantages of the invention will be apparent from the following description of particular embodiments of the invention, as illustrated in the accompanying drawings in which like reference characters refer to the same parts throughout the different views. The drawings are not necessarily to scale, emphasis instead being placed upon illustrating the principles of the invention.

FIGS. 4A-4F show leaching efficiency over time and temperature for NMC charge material samples;

DETAILED DESCRIPTION

Figure 1:
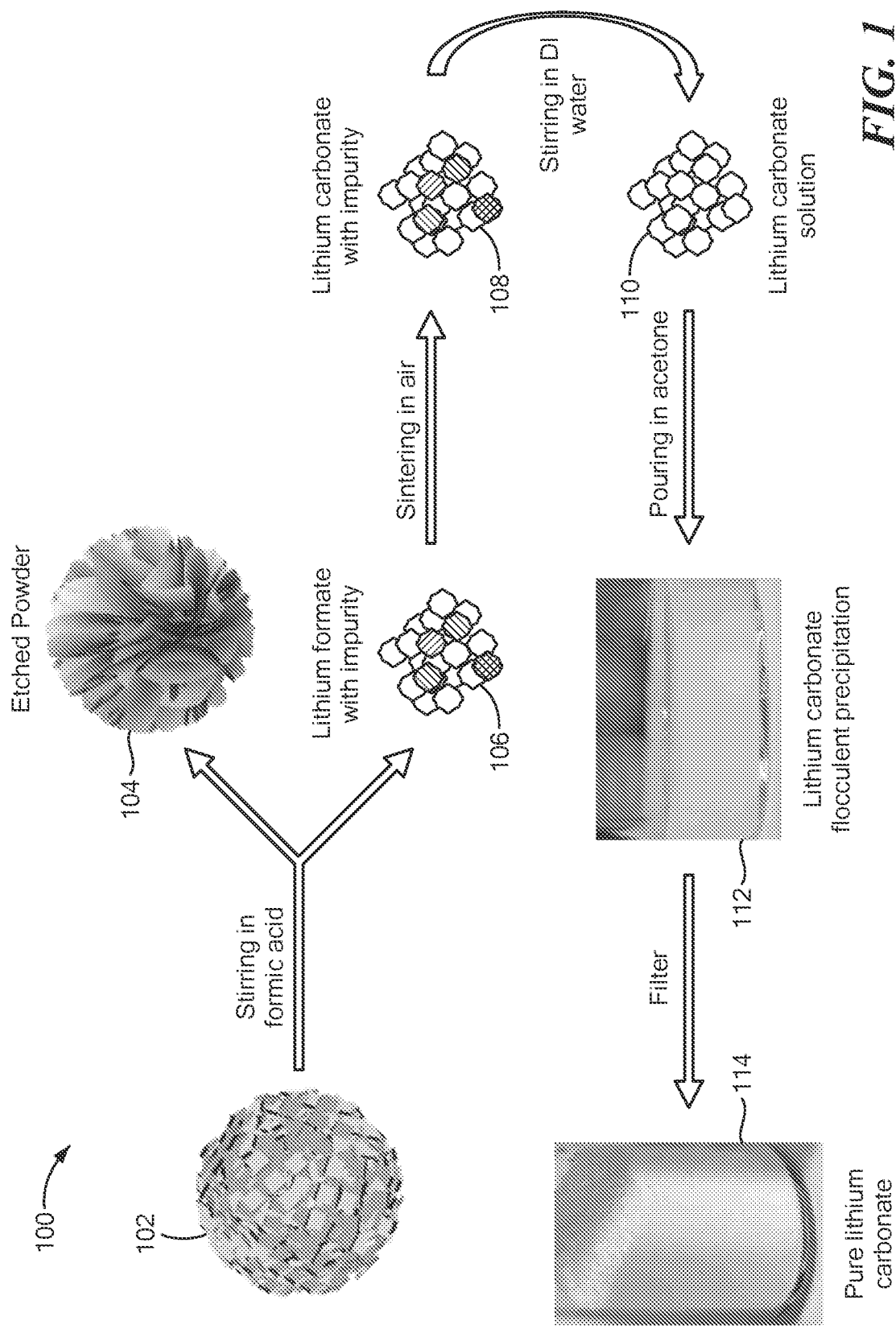
FIG. 1 is a context level diagram of the lithium recycling process as disclosed herein.

The description below presents an example of the disclosed recycling process for lithium from a lithium rich recycling stream, such as spent EV batteries, although other suitable rechargeable battery sources may also be sourced. Batteries include cathode and anode charge materials, formed in a containment including an array of cells formed by applying the charge materials to conductive sheets of current collectors, and various connectors, conductors, and casing. EVs are a particularly robust source of charge material simply due to the size of the required battery pack, whereas other uses such as cell phones, power tools and consumer devices, often strive for a smaller size. A typical EV includes about 8 kg of lithium in its battery pack.

Batteries for recycling may include not only charge material that has lost its effectiveness due to age and charging cycles, but also vehicles entering the recycling stream due to relatively new vehicles rendered unusable due to accidents, recalls, manufacturing errors and safety issues. In other words, not all the charge material is necessarily "old," but rather enters the recycling stream from a variety of sources. Physical agitation, such as crushing and shredding, removes the physical battery casing by any suitable mechanism, where the result is a granular mass of charge material that physically stores the electric charge in the batteries.

The charge material for recycling, therefore, includes anode materials, mostly carbon and graphite, and cathode materials, such as lithium metal oxide based cathode materials: NCM (Lithium Nickel Cobalt Manganese Oxide), LMO (Lithium Manganese Oxide), NCA (Lithium Nickel Cobalt Aluminum Oxide), LCO (Lithium Cobalt Oxide) and lithium polyanion type cathode materials: LFP (Lithium Iron Phosphate). In the cathode recycling stream, lithium remains combined with the transition metal component, often Ni, Mn and Co (NMC) in a ratio according to the battery chemistry, although any suitable mixture of transition metals may be employed. Conventional recycling processes seek the transition metals, as these present the most lucrative recycling potential due to the expense of mining and generating virgin materials. Recent demands, however, have demonstrated the feasibility of lithium recycling. Configurations disclosed herein selectively extract the lithium from a charge material comingled with NMC, which may or may not have undergone recycling for NMC extraction. In either case, at least a residual portion of NMC remains; the approach herein extracts substantially pure lithium without contamination by residual NMC. So-called "battery grade" materials demand such high purity.

Conventional recycling employs a pyrometallurgical approach. The pyrometallurgical recycling process usually extracts target metals via a high-temperature treatment. Although it is simple and easy to scale up, lithium remains challenging to be recovered effectively and often remains in the slag of the process. More recently, however, some researchers have investigated further on recycling lithium from the slag via a hydrometallurgy method.

In contrast, the hydrometallurgical recycling process uses an aqueous chemical method to decompose target elements into solution. In this conventional process, lithium is often extracted last in the solution. A particular conventional approach recycled 75% of lithium at the end of the hydrometallurgy process via adding a saturated $Na_2CO_3$ solution. Others reported a similar work with a recovery rate of 91.23% for lithium. Although the recovery rate is high for both two methods, the extra oxidant and precipitant increase the cost of the recovery process and adds an additional burden for the environment. While the hydrometallurgical process has a high recovery rate of lithium, the low concentration of lithium in the raffinate requires an extra concentration process, leading to a high back-end cost. Another direct recycling process is a recovery method that directly harvests and recovers active materials from LIB s, while retaining their original compound structure. During this process, lithium is not extracted from spent cathode materials. Extra Li sources will be added to recover the structure and performance of spent cathode materials. In summary, despite the increased interest in lithium recycling, substantial challenges of the commercialization aspects and development of a feasible and sustainable process still remain.

The approach discussed further below presents a highly selective process of lithium extraction via concentrated formic acid leaching. In this process, lithium is preferentially extracted with only a trace amount of transition metals (<5%) leached into the solution. The optimized condition is obtained at 60° C. for 5 hours. In addition, related chemicals can be reused via a facile distillation process, thereby allowing a fully closed-loop process for environmentally benign lithium recovery. With the disclosed method, lithium can be 100% leached from different layered oxide cathode materials where the purity of recovered lithium carbonate can reach as high as 99.994% with 99.8% recovery efficiency.

FIG. 1 is a context level diagram of the lithium recycling process as disclosed herein. In a battery recycling environment for rechargeable cells, a method for selective recovery of charge materials from a recycling stream including transition metals commences by dissolving a lithium based charge material in an organic acid having a resistance or suppression of dissolution of transition metals, as shown at step 102. Selective leaching occurs in a containment or vessel while stirring to ensure good contact area between the cathode materials and organic acid. The leaching process involves selecting the organic acid based on an ability to dissolve the lithium while the charge materials remain insoluble in the organic acid. In the approach herein, formic acid was selected for an ability to form an insoluble coating around the transition metals in the recycled charge material while leaching substantially all of the lithium.

After leaching, the solid powder was separated from the leaching solution through filtering as an etched powder, as shown at step 104. Then, the leaching solution was distillated at the set temperature while stirring to recycle the formic acid whereas contaminated lithium formate was collected for further recovery and purification, as depicted at step 106. This involves distilling a leach solution formed from the dissolved charge material for generating a powder including lithium and trace impurities of the transition metals. The contaminated lithium formate was sintered in a muffle furnace, as the sintering process was carried out under an ambient air atmosphere, as disclosed at step 108. The heating and cooling rates during sintering were maintained at 2° C./min. Sintering the generated powder forms lithium carbonate and carbonates of the trace impurities. The sintered powder was dissolved in deionized water (DI water) at room temperature. This allows recovery of the lithium carbonate by adding deionized water to the sintered powder for dissolving the lithium carbonate resulting in a lithium carbonate solution. After filtering, the lithium carbonate solution was collected, as depicted at step 110. The NMC carbonates define trace impurities that are insoluble in water, such that the lithium carbonate is recoverable by water washing. Addition of a precipitation agent to the lithium carbonate solution precipitates the lithium carbonate. In the example shown, the lithium carbonate was precipitated when transferring the solution into acetone, as depicted at step 112. The recovered lithium carbonate powder was filtered and dried to generate substantially pure lithium carbonate, as shown at step 114. To purify the used acetone solution, a distillation process was performed based on boiling point for complementing the closed loop aspect.

The examples above employed formic acid (98%), Acetone (≥99.5%) and commercial lithium carbonate ($Li_2CO_3$). The chemistry of the charge material includes $LiNi_{1/3}Mn_{1/3}Co_{1/3}O_2$ (NMC111), $LiNi_{0.6}Mn_{0.2}Co_{0.2}O_2$ (NMC622), $LiNi_{0.8}Mn_{0.1}Co_{0.1}O_2$ (NMC811), and black mass (actual spent LIBs powder including mixed cathode materials, graphite, and conductive carbon) for use in the leaching process. All used materials were dissolved in the acid solution to validate the stoichiometric ratio of the elements by inductively coupled plasma-optical emission spectrometry (ICP-OES).

Figure 2:
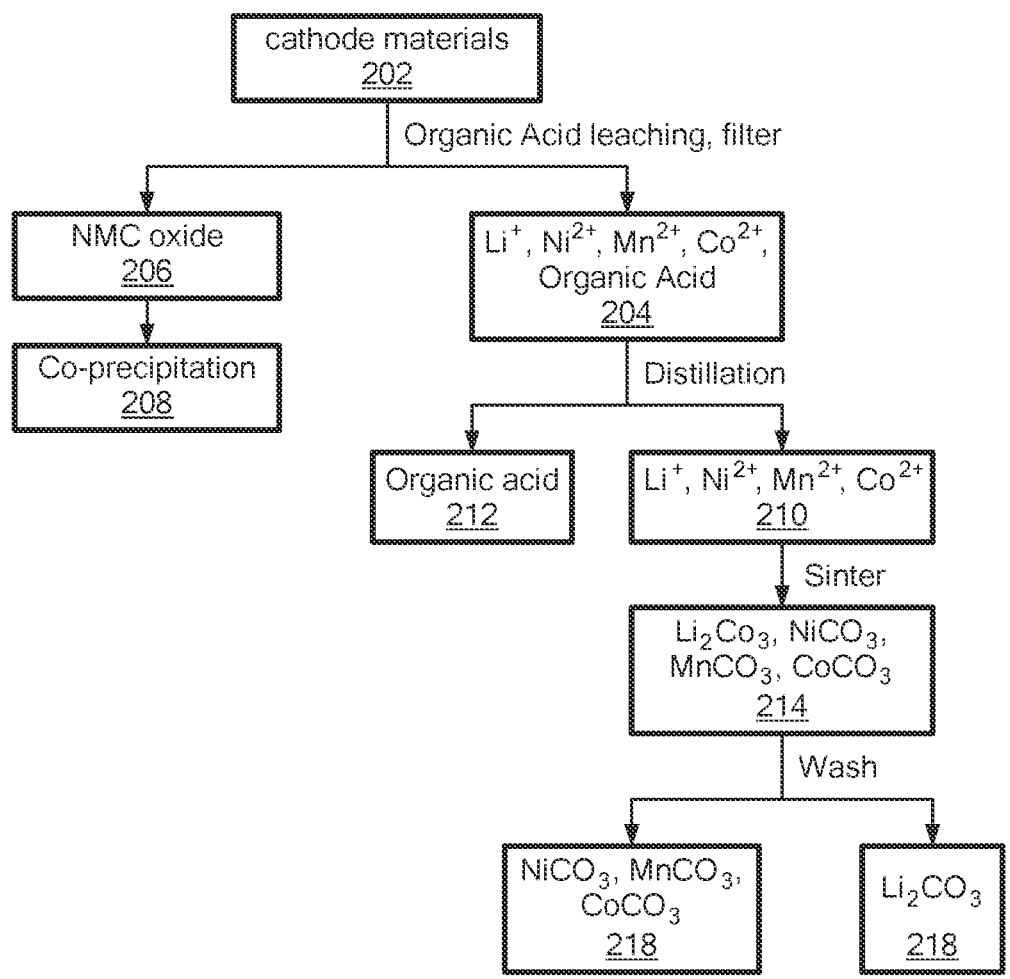
FIG. 2 is a flowchart of the recycling process of FIG. 1.

FIG. 2 is a flowchart of the recycling process of FIG. 1. Referring to FIGS. 1 and 2, in a specific configuration, formic acid can be used to selectively leach lithium out from the cathode materials because lithium formate is soluble in the concentrated formic acid whereas the transition metals (TM) formate is insoluble in the concentrated formic acid. To investigate the optimized conditions for formic acid leaching, for all the layered oxide cathode materials, the effects of reaction time and temperature may be varied accordingly, discussed further below.

A particular example of the method for recycling pure lithium from a recycling stream of batteries includes forming a leach solution of charge material and formic acid. At step 202, the cathode charge material including lithium and transition metals including Ni, Mn and Co (NMC) are leached by heating the leach solution to around 60° C. for dissolving the lithium and forming dissolution-resistant formate salts on a particle surface of the transition metals, as shown at step 204. Separated NMC oxides and TM formate from the recycling stream at step 206 may be recovered by further extraction, at step 208. The leach solution is distilled for generating a powder of lithium formate and trace quantities of transition metal formate salts from the remaining NMC, as disclosed at step 210. The organic acid (formic acid) may be reused for successive leaching cycles, depicted at step 212. The generated powder is sintered in atmospheric conditions for forming lithium carbonate and Ni, Mn and Co carbonates, at step 214. The powder is washed in deionized water for dissolving the lithium carbonate in a lithium carbonate solution, at step 216, while the Ni, Mn and Co carbonates remain in powder form at step 218. The lithium carbonate solution is combined with acetone for forming a flocculant precipitation, and the precipitated lithium carbonate is extracted to define at least 99% of the lithium in the charge material.

Particular configurations may include heating the leach solution formed from the dissolved lithium-based charge material for increasing a leaching efficiency of the lithium, while allowing formation of salts on the transition metals for inhibiting dissolution of the transition metals. To determine the temperature for the reaction, the leaching time is fixed at 1 hour. $LiNi_{1/3}Mn_{1/3}Co_{1/3}O_2$ (NMC111) was first applied to examine the appropriate temperature condition. The leaching efficiency of lithium is only 67.5% at 20° C. Then, the leaching rate of lithium increases gradually with the increased temperature and reaches 100% at 60° C. However, when the temperature increases to 70° C., the leaching efficiency decreases to 89.7% and further decreases to 87.1% at 80° C. This is due to adhesion of the insoluble salts on particle surfaces that prevent the leaching process.

Figure 3A:
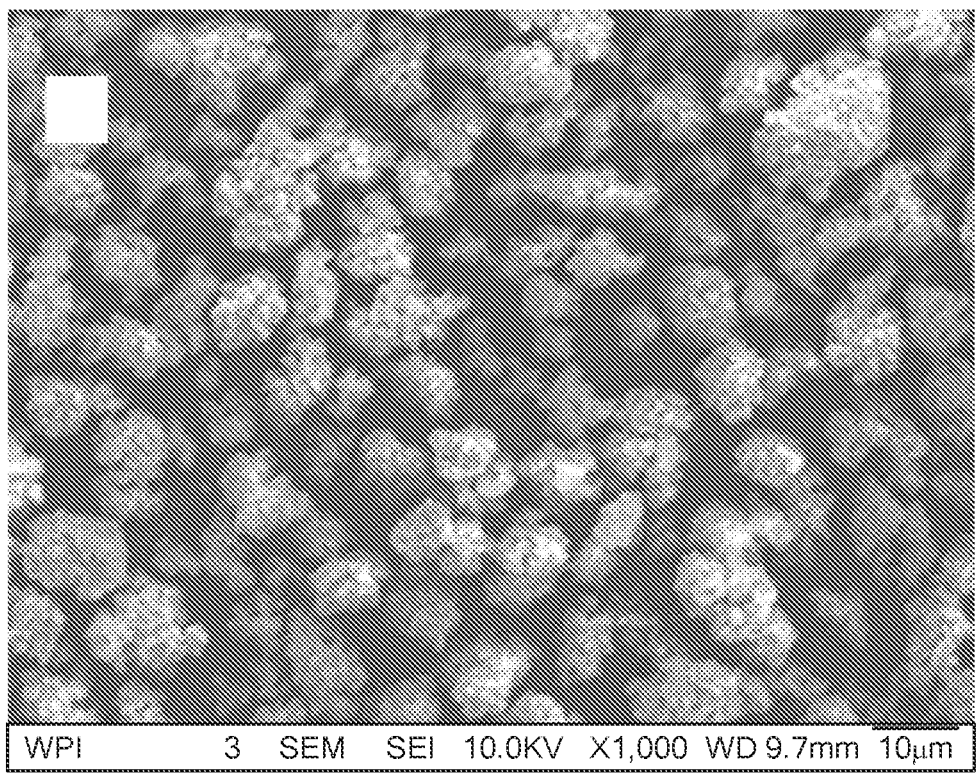
FIGS. 3A-3H show SEM (Scanning Electron Microscope) images of leached particles and the insoluble salt shell thereon.
Figure 3B:
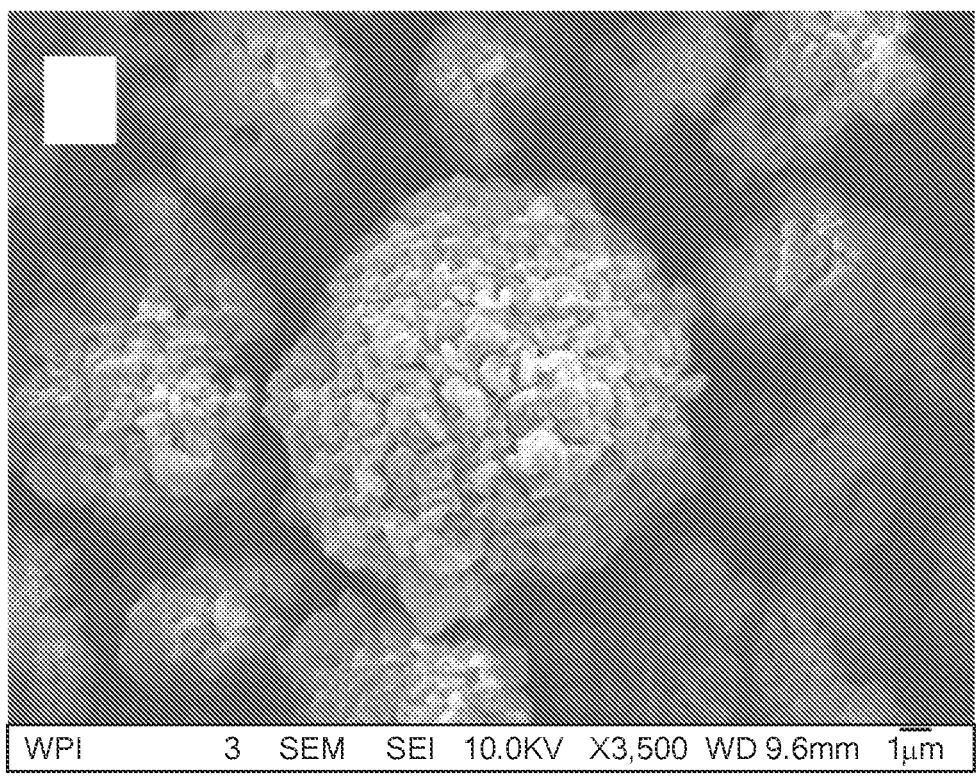
Figure 3C:
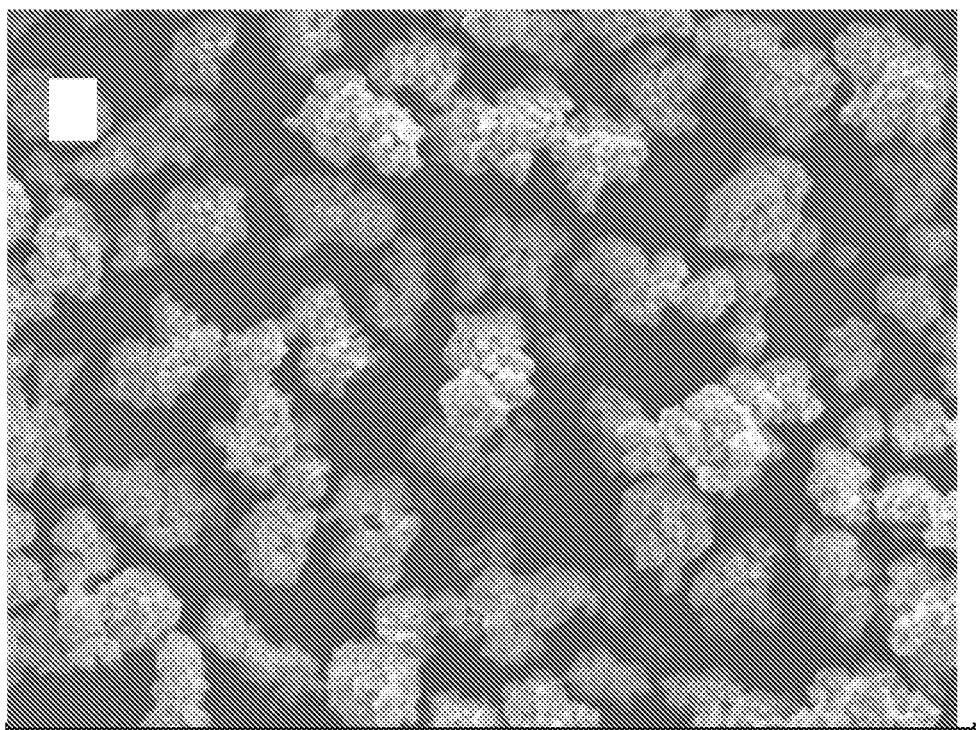
Figure 3D:
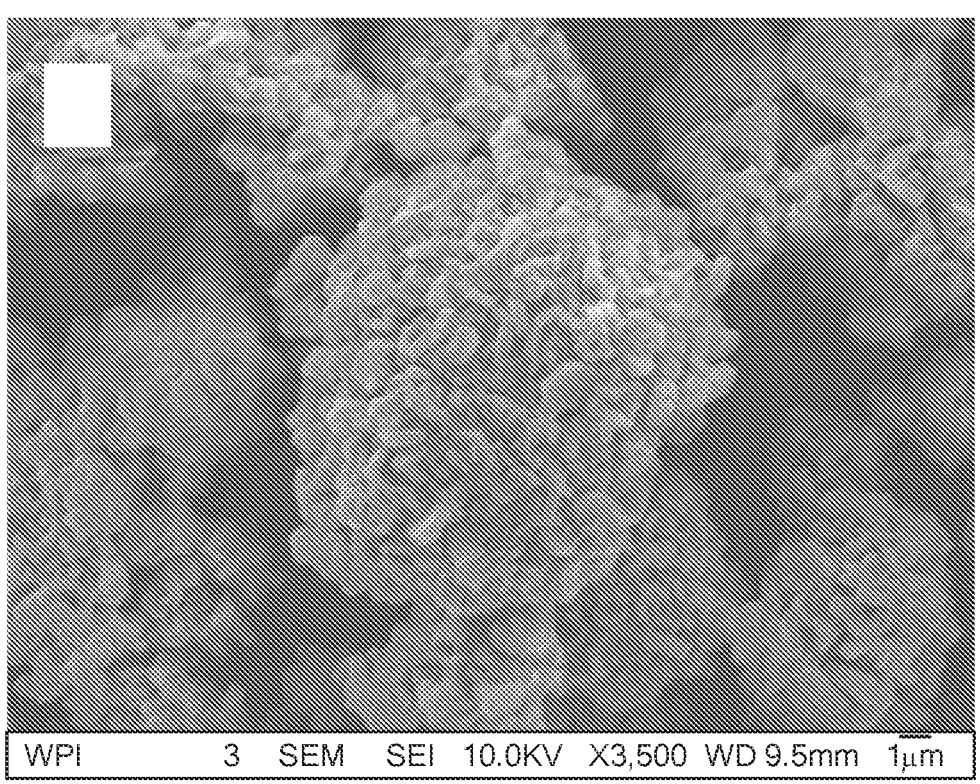
Figure 3E:
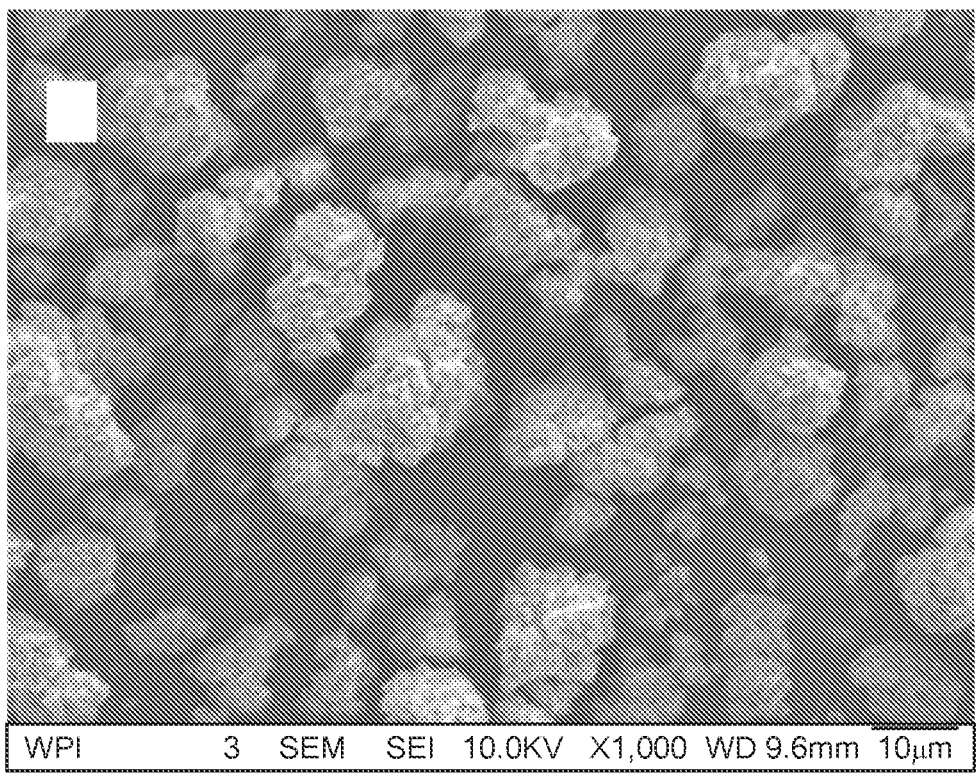
Figure 3F:
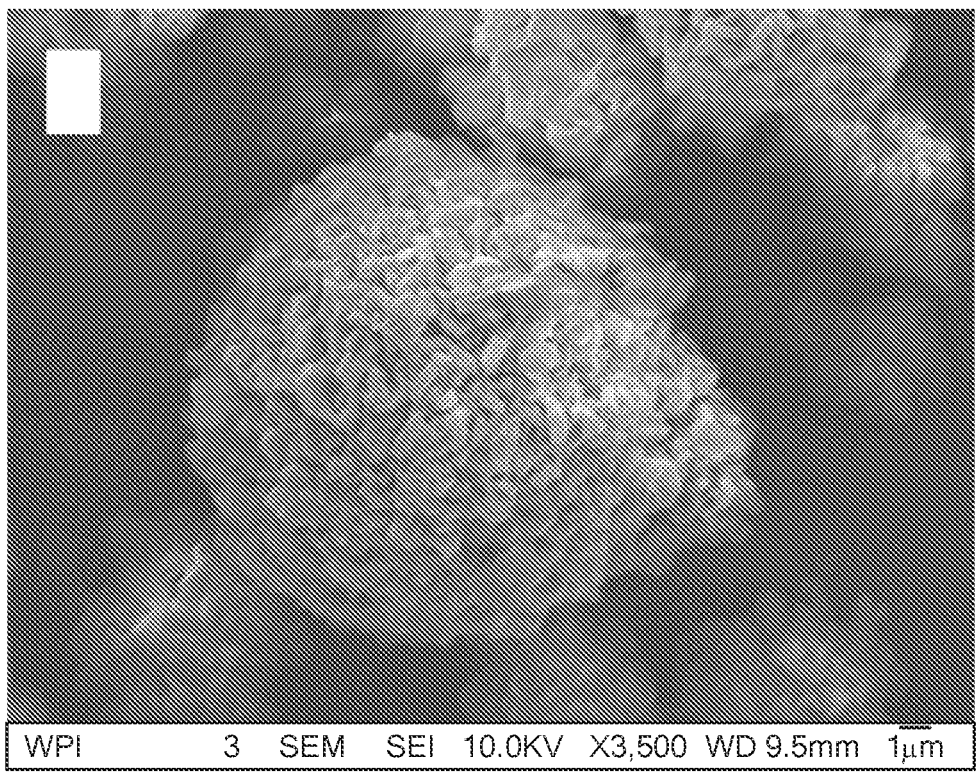
Figure 3G:
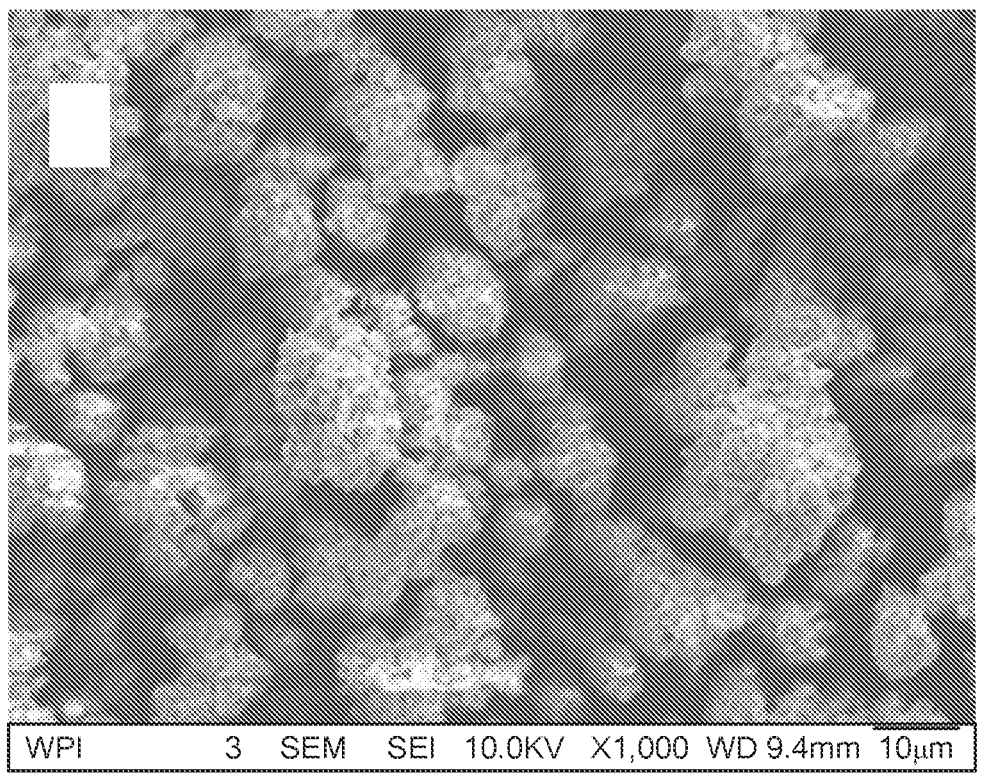
Figure 3H:
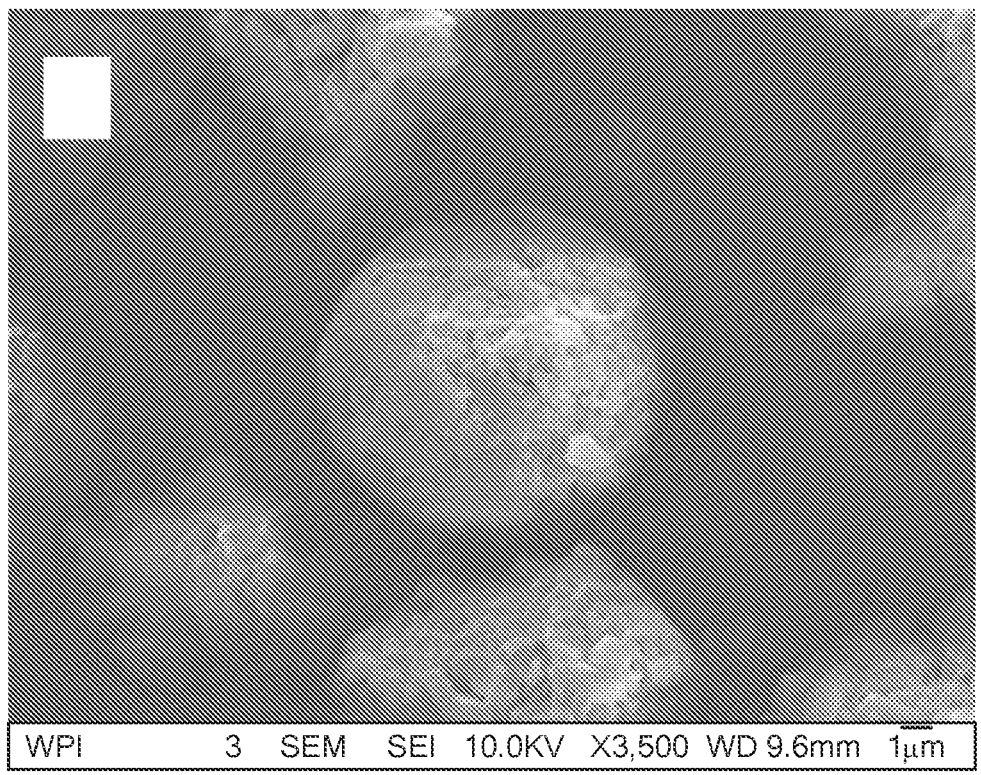

FIGS. 3A-3H show SEM (Scanning Electron Microscope) images of leached particles and the insoluble salt shell thereon. In FIGS. 3A-3H the shell of TM salts can be seen clearly, and its thickness is increased as temperature increases. Moreover, FIGS. 9A and 9B, discussed below, exhibit the morphology of etched NMC111 particles before and after water washing process. Before water washing, the etched powder still has large primary particles and dense secondary particles. However, after water washing, the large primary particles are generally unobservable, and the secondary particles show a significant porous structure, discussed further below with respect to FIGS. 9A and 9B. This is because the large primary particles are TMs formate salt particles, which are insoluble in concentrated formic acid. As a result, TMs formate salts will form on the particle surface and prevent the leaching process. Although the leaching rate of TMs has similar trend as lithium, it is under 5% at any given temperature. Therefore, 60° C. is the optimized temperature for NMC111 to completely leach lithium out. The progression is shown in FIGS. 3A-3H. FIG. 3A is the aggormeration of leached particles at 50° C. for 1 hr; FIG. 3B shows the insoluble salt shell formed on the surface of the particles at 50° C. for 1 hr; FIG. 3C is the aggormeration of leached particles at 60° C. for 1 hr; FIG. 3D shows the unsoluable salt shell formed on the surface of the particles at 60° C. for 1 hr; FIG. 3E is the aggormeration of leached particles at 70° C. for 1 hr; FIG. 3F shows the insoluble salt shell formed on the surface of the particles at 70° C. for 1 hr; FIG. 3G is the aggormeration of leached particles at 80° C. for 1 hr; and FIG. 3H is the insoluble salt shell formed on the surface of the particles at 80° C. for 1 hr.

Figure 4F:
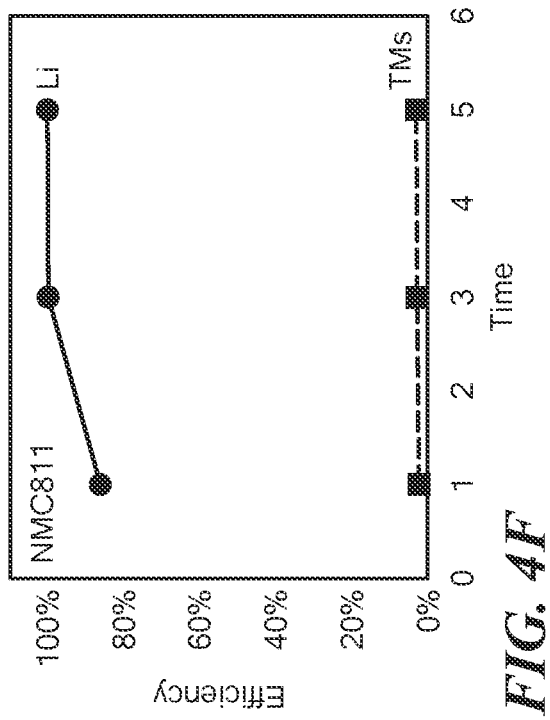

FIGS. 4A-4F show leaching efficiency over time and temperature for NMC charge material samples. In FIG. 4A, as indicated above, 60° C. is the optimized temperature for NMC111 to completely leach lithium out (upper line), while trace impurities of transition metals (TMs) are shown by the lower line. Subsequently, $LiNi_{0.6}Mn_{0.2}Co_{0.2}O_2$ (NMC622) and $LiNi_{0.8}Mn_{0.1}Co_{0.1}O_2$ (NMC811) were tested at 50° C., 60° C., 70° C. and 80° C. based on the results of NMC111. As shown in FIG. 4B, the leaching efficiency of lithium for NMC622 at 50° C., 60° C., 70° C. and 80° C. is 38.01%, 66.51%, 60.41% and 45.60% whereas the leaching efficiency of TMs is 1.30%, 1.52%, 1.10% and 1.27% respectively. In FIG. 4C, the lithium leaching efficiency for NMC811 at 50° C., 60° C., 70° C. and 80° C. is 49.2%, 86.55%, 81.42% and 55.63% with leaching efficiency of TMs is 1.53%, 2.97%, 2.59% and 1.98%, respectively. Thus, 60° C. is demonstrated as the optimized temperature.

Figure 4E:
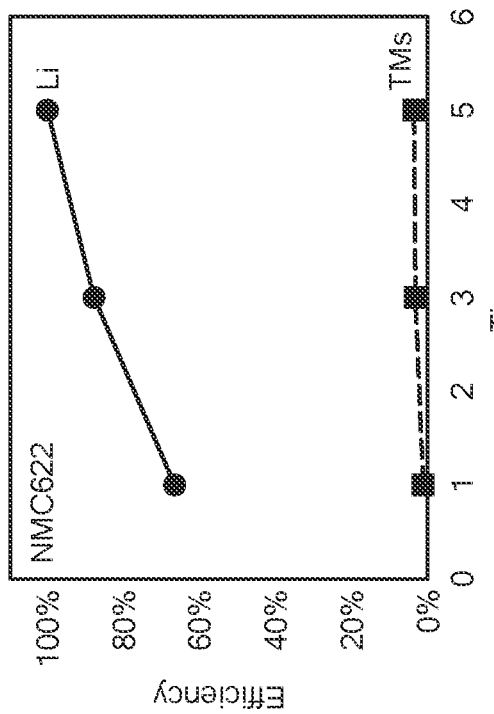

The effect of reaction time on leaching efficiency of metals was examined at fixed solid-to-liquid ratio of 20 and temperature of 60° C. In FIGS. 4D-4F, the leaching efficiency of all metals keeps increasing as the time extends. In fact, the leaching efficiency of lithium for NMC111 is 100% since the first hour (FIG. 4D), however, the leaching efficiency of NMC622 and NMC811 is only 66.51%, and 86.55% after 1 hour, respectively (FIGS. 4E, 4F). After 3 hours, the leaching percentage of lithium for NMC622 is increased to 92.10%, and the leaching percentage of NMC811 increases to 100%. Furthermore, as the time increases to 5 hours, the leaching efficiency of lithium increases to 100% with 3.96% of transition metals leaching efficiency for NMC622, and 3.34% for NMC811.

Figure 5A:
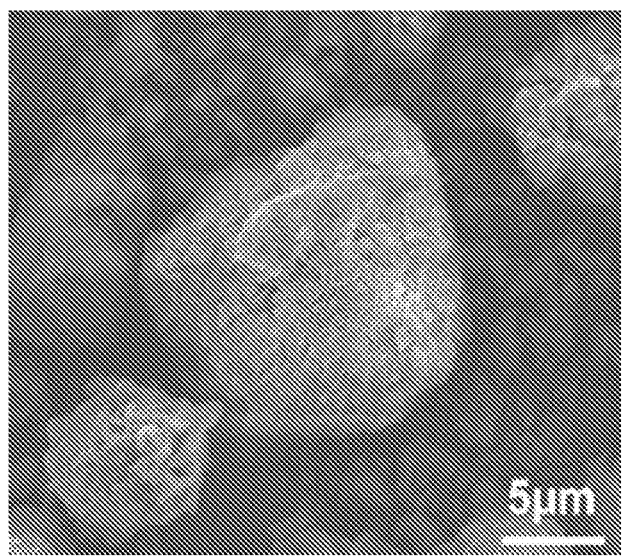
FIGS. 5A-5C show SEM images of the corresponding NMC particles of FIGS. 4A-4F.
Figure 5B:
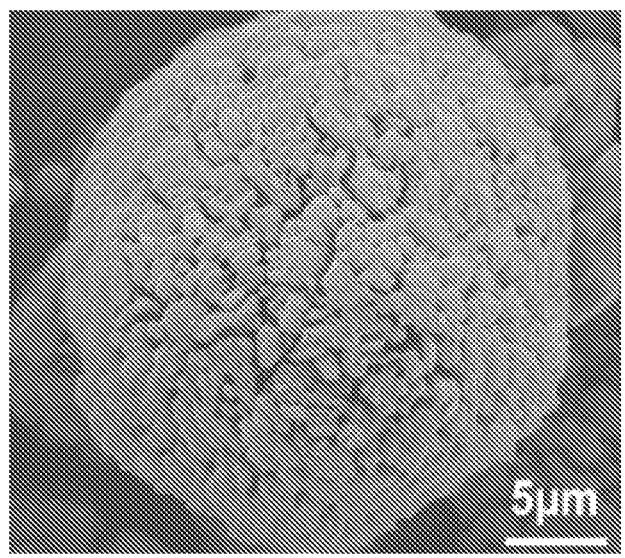
Figure 5C:
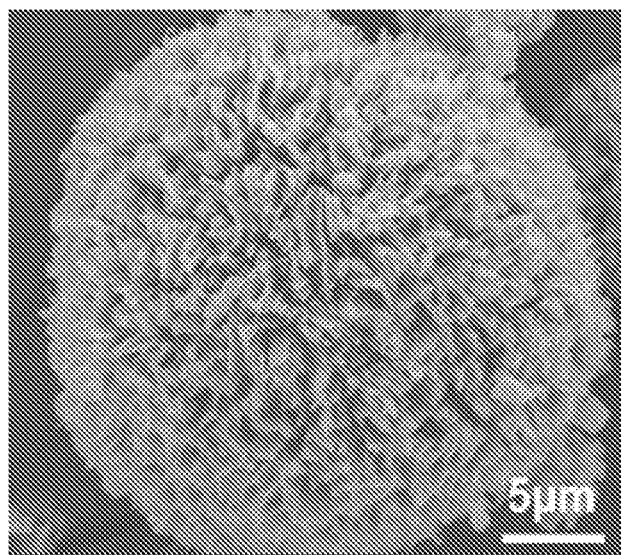

FIGS. 5A-5C show SEM images of the corresponding NMC particles of FIGS. 4A-4F. As shown in FIG. 5A, the NMC111 particles are etched after reacting with the formic acid. As time increases, the particles become more porous as shown in FIGS. 5B and 5C, which indicates that both the lithium and TMs are leached out. In short, the optimized leaching conditions are at 60° C. for 5 hours where the leaching efficiency of NMC111, NMC622, and NMC811 are all 100% for lithium with less than 5% of TMs.

By considering the reality of recycling manufacturing, the cathode powders are typically mixed with different cathode materials, anode powder and carbon black. Thus, to study the effect of mixed powder, two samples including a mixture of NMC111, NMC622 and NMC811, and black mass (actual spent LIBs powder composed of NMC111, $LiMn_2O_4$, graphite anode and conductive carbon) are leached at 60° C. for 5 hours and the results have been summarized in FIG. 6.

Figure 6:
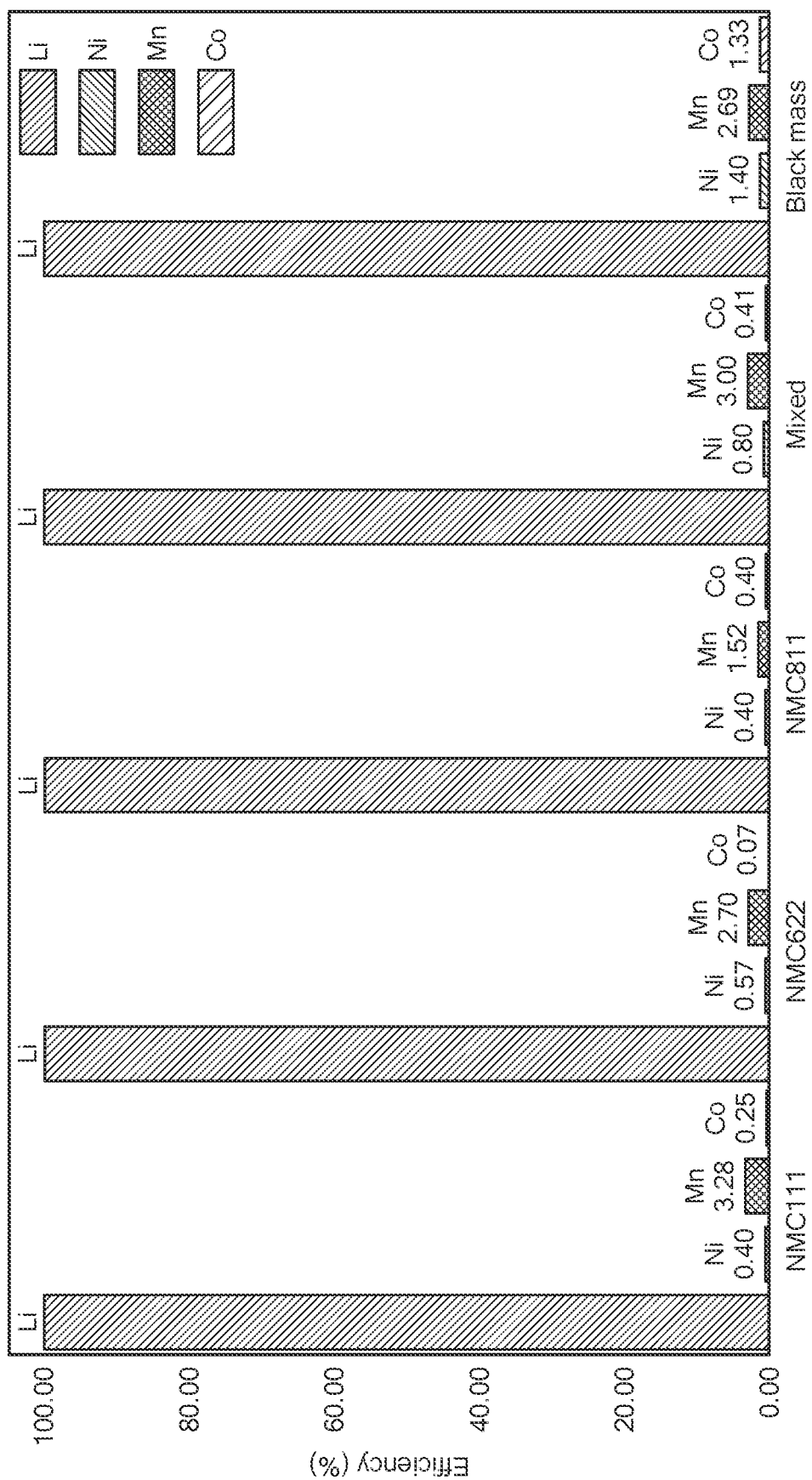
FIG. 6 shows leaching efficiency using formic acid as the organic acid for leaching as in FIGS. 1-5C.

FIG. 6 shows leaching efficiency using formic acid as the organic acid for leaching as in FIGS. 1-5C. Referring to FIG. 6, remarkably, the leaching efficiency of lithium for all tested materials can reach 100%, and the leaching efficiency of TMs for mixed cathode materials and black mass were 4.21%, and 5.42%, respectively. In general, the leaching rate of Ni and Co is under 1.5% and the leaching efficiency of Mn is under 3.5%, which considered to be only trace amount.

Figure 7:
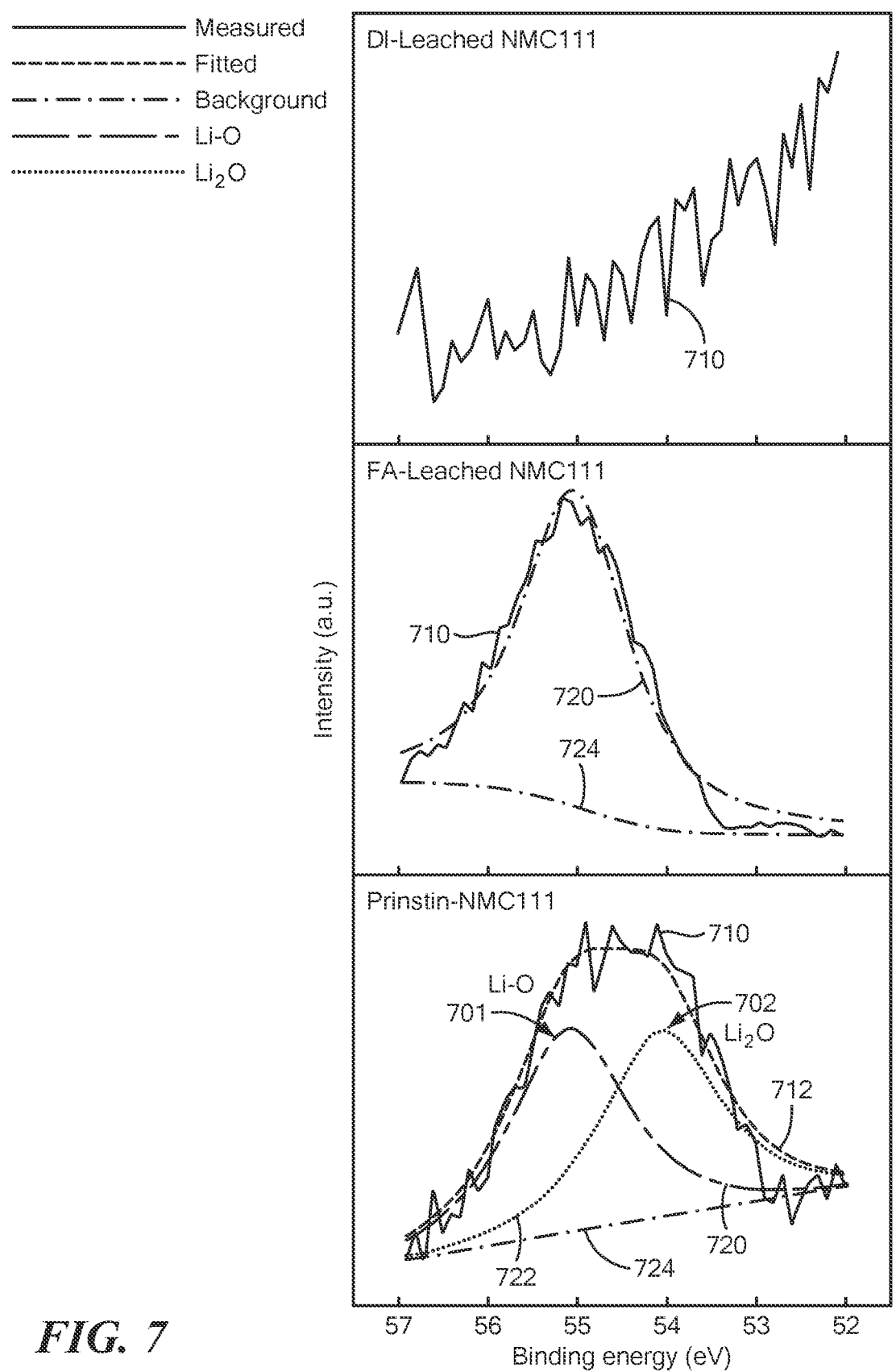
FIG. 7 shows X-ray photoelectron spectroscopy (XPS) measurements indicative of an oxidation state at the particle surface during leaching.

FIG. 7 shows X-ray photoelectron spectroscopy (XPS) measurements indicative of an oxidation state at the particle surface during leaching. X-ray photoelectron spectroscopy (XPS) measurements were carried out to investigate the oxidation state of lithium and transition-metals (Ni, Mn, and Co) at the particle surface during the leaching process. Measured intensity 710 for the respective NMC sources is shown, approximated by a fitted curve 712. LiO 720 is shown along with $Li_2O$ 722, and background readings 724 for comparison. The binding energy for C1s was found as, for Pristine-NMC111, 284.87 eV; FA(Formic Acid)-Leached NMC111 as 284.76 eV; and DI-Leached NMC111 as 284.91 eV, used to perform calibration for all other elements. As shown in FIG. 7, there are two peaks 701, 702 located at 54.07 eV, and 55.1 eV in pristine NMC111 cathode materials, which demonstrates that the existence of $Li_2O$ in NMC111 crystal structure and residual $Li_2CO_3$ on the surface of NMC111.

Figure 8:
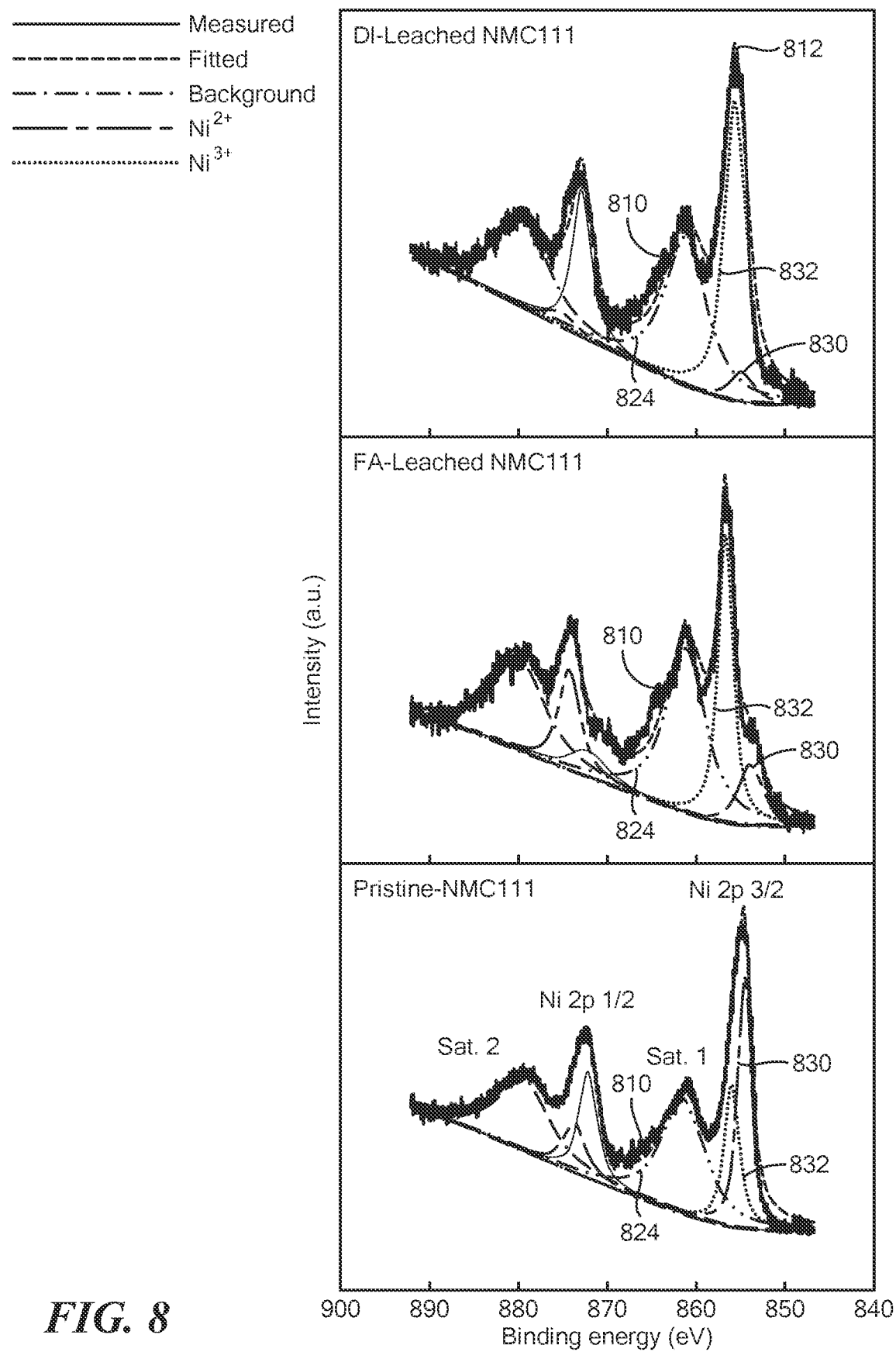
FIG. 8 shows XPS measurements of NMC indicating a lithium-oxide bond Li—O contributed by the formic acid.

FIG. 8 shows XPS measurements of NMC indicating a lithium-oxide bond Li—O contributed by the formic acid. A measured intensity 810 is approximated by a fitted curve 812. $Ni^{2+}$ 830 is shown with $Ni^{3+}$ 832 and background levels 824. For leached NMC111 particles washed by formic acid (FA-Leached NMC111), the lithium oxide bond (Li—O) can still be detected at 55.0 eV (FIG. 8), which is contributed by lithium formate. The ICP results shows that approximate 0.1% lithium can still be detected in FA-Leached NMC111. During leaching, NMC111 particles reacted with formic acid producing nickel(II) formate, which is insoluble in the concentrated formic acid.

Figure 9A:
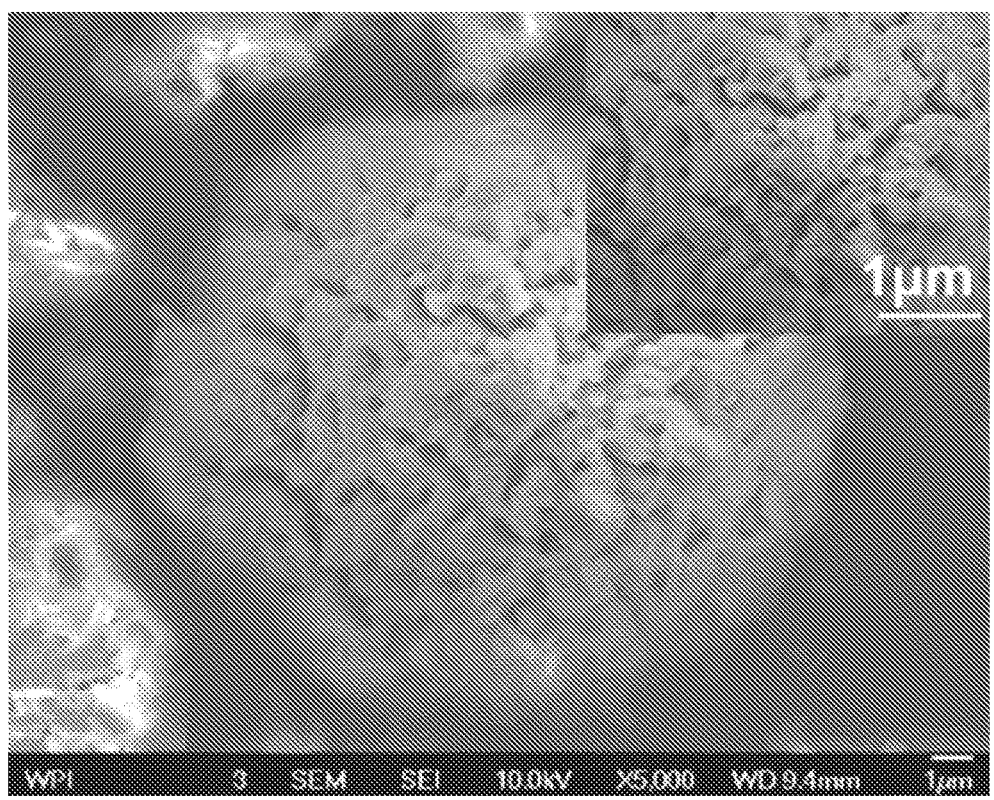
FIGS. 9A and 9B show particles after leaching treatment and water washing.
Figure 9B:
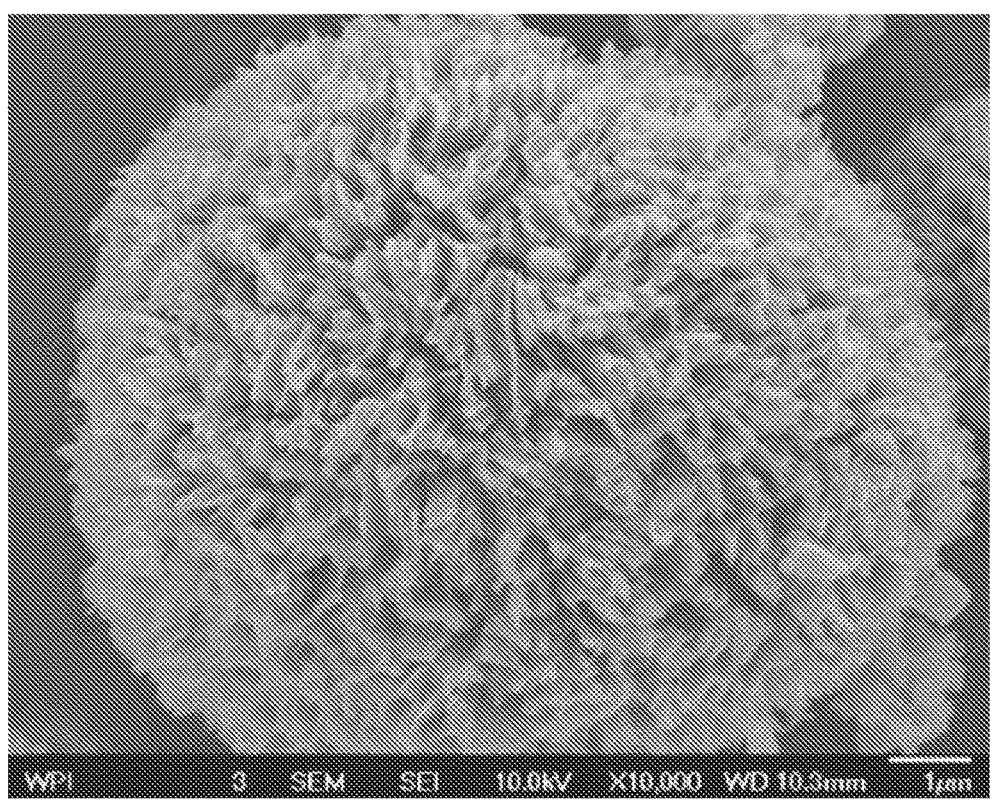
Figure 10A:
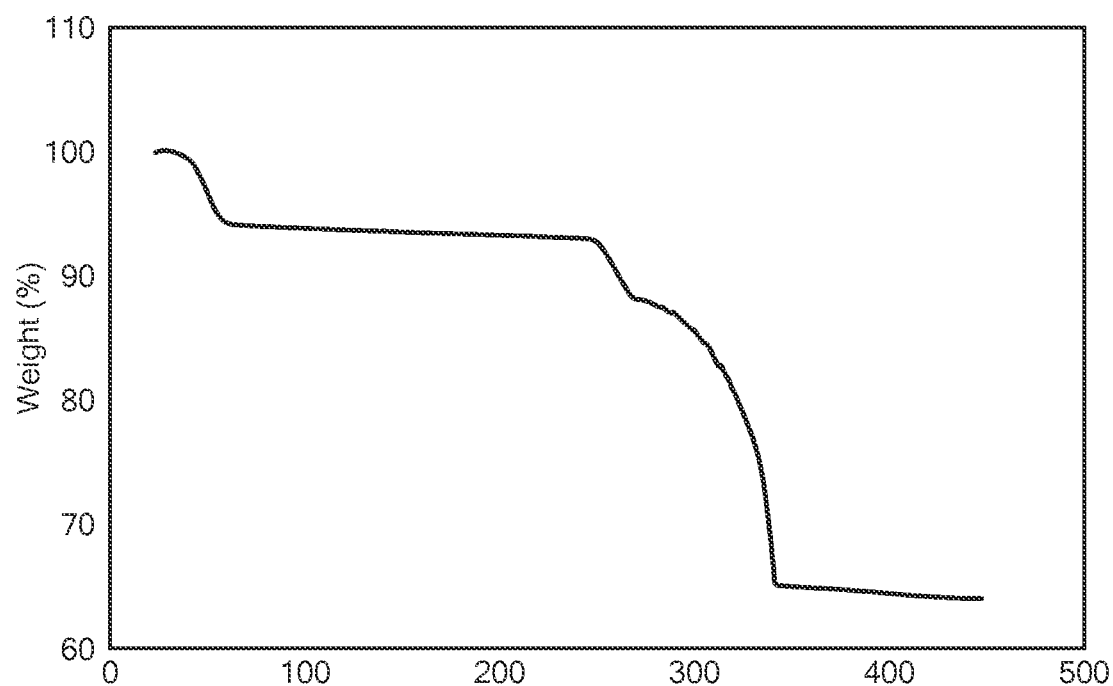
FIGS. 10A-10D show TGA (Thermal Gravimetric Analysis) of the recovered lithium carbonate.
Figure 10B:
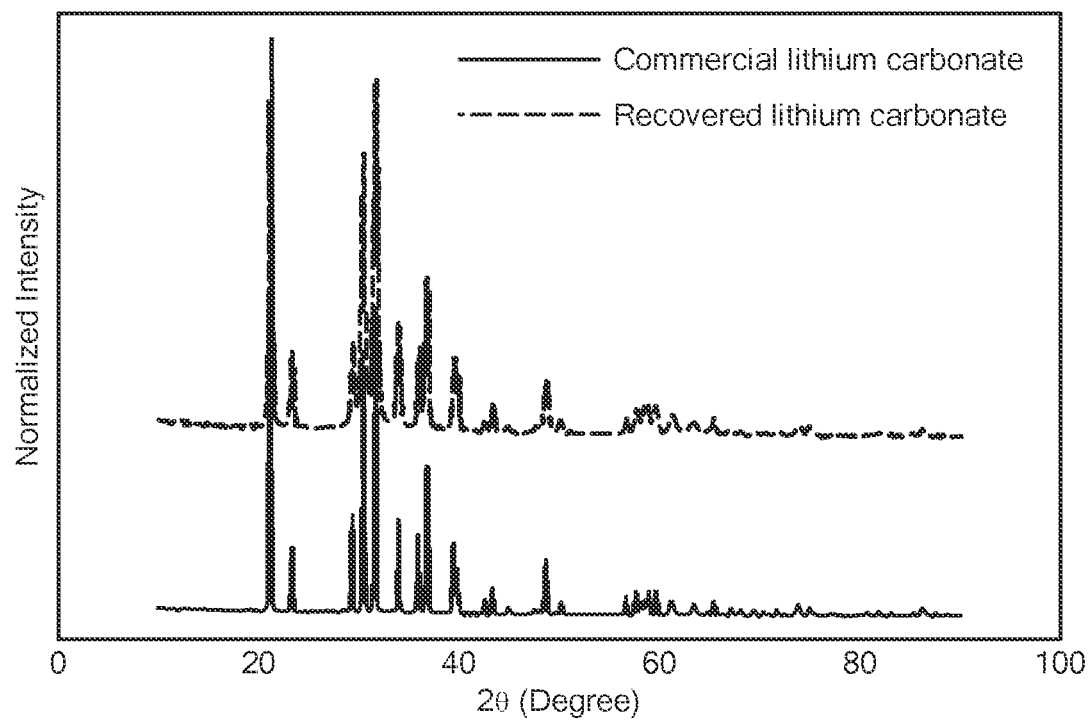
Figure 10C:
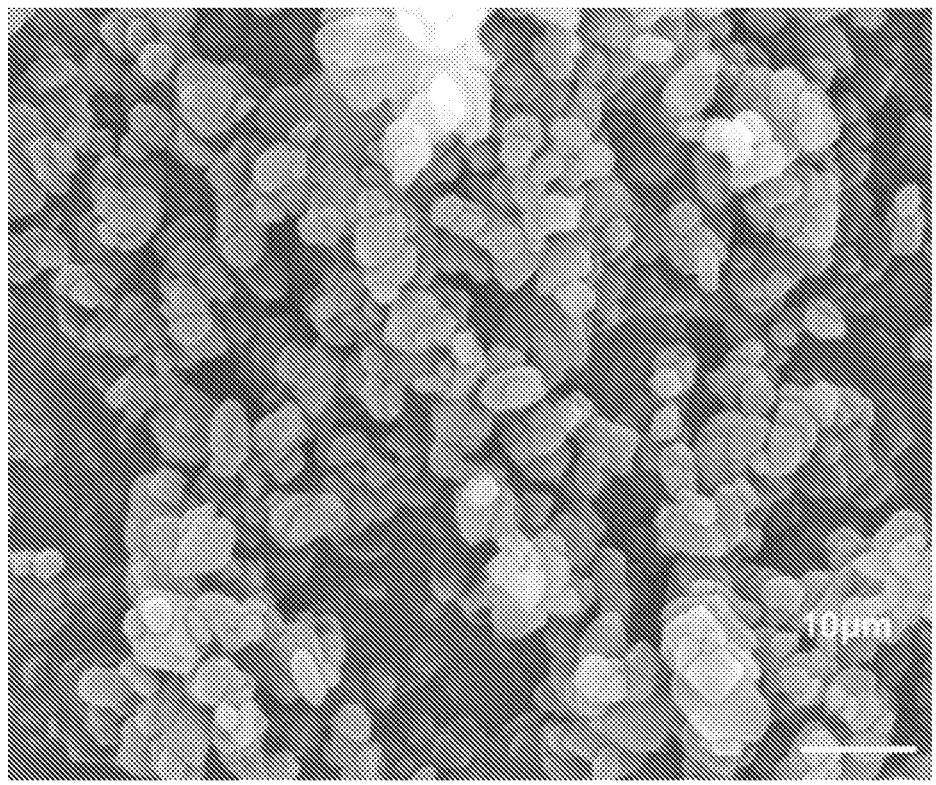
Figure 10D:
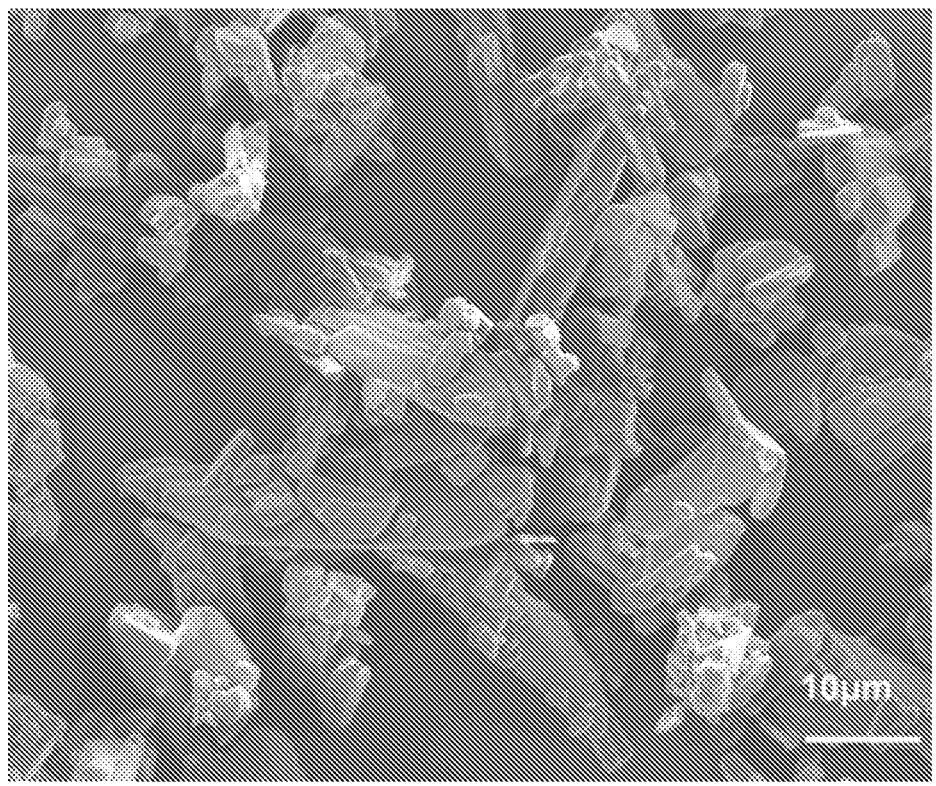

FIGS. 9A and 9B show particles after leaching treatment and water washing. The morphology of etched NMC111 particles before and after water washing process shows that before water washing, the etched powder still has large primary particles and dense secondary particles as shown in FIG. 9A. However, after water washing, the large primary particles are unobservable, and the secondary particles show a significant porous structure as shown in FIG. 9B. This is because the large primary particles are TMs formate salt particles, which are insoluble in concentrated formic acid. As a result, TMs formate salts will form on the particle surface and prevent the leaching process. Although the leaching rate of TMs has similar trend as lithium, it is under 5% at any given temperature FIGS. 10A-10D show TGA (Thermal Gravimetric Analysis) of the recovered lithium carbonate. After lithium is leached into the solution with minor formation of TMs formate, the lithium is extracted and purified as $Li_2CO_3$ by a simple distillation and sintering process. During distillation, the formic acid is evaporated from the flask, and then collected after being condensed in the condenser. In the example NMC configuration, the formate salts including lithium formate, manganese formate, cobalt formate, and nickel formate are crystallized and collected from the flask. Then, formate salts are decomposed in the sintering process and converted to the mixture of lithium carbonate, manganese carbonate, cobalt carbonate, and nickel carbonate. In order to confirm the transformation, TGA is employed to investigate the decomposition temperature for the mixture of formate salts. In FIG. 10A the weight starts dropping at 30° C. due to the dehydration of the formate salts. The second drop occurs at around 230° C., caused by the decomposition from formate to carbonate. The weight continues decreasing until around 350° C. where the decomposition of lithium formate is completed. The TMs formate converts to carbonate in the range of 230° C. to 340° C. Therefore, the obtained formate mixture is sintered in a two-step procedure. In the first step, the mixture is sintered at 350° C. for 5 hours to convert the lithium formate to lithium carbonate. Then, the temperature is further increased to 450° C. in the second step, to ensure all TMs formate is decomposed to insoluble TMs carbonate. Therefore, after the sintering process, the lithium carbonate is soluble in the DI water, and the insoluble TMs carbonate is filtered out. Then, the lithium carbonate solution is poured into acetone, due to the insolubility of lithium carbonate in acetone. Lithium carbonate forms flocculent precipitation at the bottom of the container. After filtered, the pure lithium carbonate can be obtained. As shown in FIG. 10B, the XRD pattern of the recovered lithium carbonate agrees well with the commercial lithium carbonate and no impurity peaks are observed. To compare the morphology of the recovered lithium carbonate and commercial carbonate, SEM is utilized. FIG. 10C shows the particle size of the recovered lithium carbonate is ~100 nm and has a significant agglomeration. Compared with the commercial lithium carbonate in FIG. 10D, the particle size distribution of the recovered lithium carbonate is more uniform, which may provide better dispersion when mixing with the precursor. Further, the final recycling rate of lithium reaches 99.8%, which is substantially higher than conventional approaches.

ICP-MS is employed to detect the purity of the recovered lithium carbonate where the commercial lithium carbonate is tested as a reference. Same amounts of the recovered lithium carbonate and commercial lithium carbonate are dissolved in aqua regia solution for ICP-MS testing. Compared to the commercial lithium carbonate, the amount of impurity elements in the recovered lithium carbonate is much lower, indicating a higher purity. Based on the equation below, the calculated purity of the recovered lithium carbonate is 99.994%.

$$\text{Purity} = \frac{\text{Tested concentration of lithium carbonate}}{\text{Actual weight of lithium carbonate powder}} * 100\%$$

For a deeper quality analysis, a batch of $LiNi_{0.33}Mn_{0.33}Co_{0.33}O_2$ (RLi-NMC111) cathode material was synthesized with the recovered lithium carbonate. A typically spherical secondary particle consisting of primary particles was observed. The particle size for Commercial-NMC111 is ~21.59 μm, and for RLi-NMC111 is ~20.76 μm. The phase and structure of Commercial-NMC111, and RLi-NMC111 were analyzed, and the XRD pattern of RLi-NMC111 matched well with Commercial-NMC111, which refers to a typical layered structure. It is worth to emphasize that RLi-NMC111 has higher (003)/(104) ratio (1.79), while Commercial-NMC111 is 1.63, indicating a lower cation mixing of the RLi-NMC111 cathode material. Therefore, the RLi-NMC111 cathode material is expected to have a better electrochemical performance. To obtain the lattice data for RLi-NMC111 and Commercial-NMC111, the refinement was used to calculate the structure parameters. Compared to Commercial-NMC111 cathode, the RLi-NMC111 manifested the analogous parameters indicated that the RLi-NMC111 sintered by recovered lithium carbonate can reach the comparable performance.

The RLi-NMC111 cathode material is further tested in Li/NMC half-cell and compared with Commercial NMC111 under the same condition. The electrochemical performance comparison between RLi-NCM111 and Commercial-NMC111 cathode material was undertaken. In contrast to Commercial-NMC111, the RLi-NMC111 can provide similar initial discharge capacity (152.1 mAh/g vs. 154.7 mAh/g) at 0.1C. For high-rate performances, the comparison between RLi-NMC111 vs. TODA-NMC111 is 148.3 mAh/g vs. 148.4 mAh/g, 138.9 mAh/g vs. 140.2 mAh/g, 134.1 mAh/g vs. 134.9 mAh/g, 118.4 mAh/g vs. 120.6 mAh/g, and 111.9 mAh/g vs. 111.4 mAh/g, 102.9 mAh/g vs. 104.5 mAh/g, for 0.2C, 0.5C, 1C, 2C, 3C, and 5C respectively. The results demonstrate that the cathode material prepared with recycled $Li_2CO_3$ provide at least matched electrochemical performance compared to commercial NMC111 cathode materials.

Formic acid has been recycled and collected from the system by a facile distillation process. The density of recycled formic acid is 1.18 g/ml, which is comparable to the virgin formic acid (1.2 g/ml). The decrease in density is due to the close boiling temperature between water produced by the leaching reaction and formic acid. The boiling point of formic acid is 100.8° C., however, the formic acid-water azeotropic mixture has a boiling point at 107° C.[47]. Therefore, by introducing water in the recycled formic acid, it may be difficult to avoid small water contamination during the distillation process. To further confirm the composition of recycled formic acid, NMR is used to determine the different hydrogen bonding in the formic acid and recycled formic acid. Although the recovered formic acid contains trace metal elements, which is slightly higher than that of commercial formic acid, the recovered formic acid still has high purity. In addition, the recycle efficiency of formic acid is as high as 99.8% where the small inevitable loss is caused by the leaching and distillation processes.

While the system and methods defined herein have been particularly shown and described with references to embodiments thereof, it will be understood by those skilled in the art that various changes in form and details may be made therein without departing from the scope of the invention encompassed by the appended claims.

What is claimed is:

1. In order to efficiently recover lithium from spent lithium ion batteries or manufacturing scraps, a method for selective lithium recovery of charge materials, comprising:
   selectively dissolving lithium from the battery charge material in an acid having a resistance to dissolution of transition metals;
   distilling a leach solution formed from the dissolved charge material to generate a powder including a lithium compound and trace impurities of the transition metals; and
   sintering the generated powder to form lithium carbonate and carbonates of the trace impurities, the trace impurities insoluble in water, the lithium carbonate recoverable by water washing.

2. The method of claim 1 further comprising
   recovering the lithium carbonate by adding deionized water to the sintered powder to dissolve the lithium carbonate; and
   adding a precipitation agent to the lithium carbonate solution to precipitate the lithium carbonate.

3. The method of claim 1 further comprising adding the acid to the charge material to form an insoluble salt of the transition metals.

4. The method of claim 1 wherein an insolubility of the transition metals is based on a formation of salts on the transition metals, the salts resistant to dissolution by the acid.

5. The method of claim 3 wherein the acid is formic acid, the formic acid added to form formate salts on a surface of transition metal particles.

6. The method of claim 2 wherein the precipitation agent includes acetone.

7. The method of claim 1 further comprising heating the leach solution formed from the dissolved lithium based charge material to increase a leaching efficiency of the lithium while allowing formation of salts on the transition metals to inhibit dissolution of the transition metals.

8. The method of claim 1 further comprising selecting the acid based on an ability to dissolve the lithium while the charge materials are insoluble in the acid.

9. The method of claim 1 further comprising selecting the acid to leach substantially all the lithium in the charge material and leaching less than 5% of transition metals in a resulting leach solution.

10. The method of claim 1 wherein distilling further comprises distilling the leach solution to remove moisture and resulting in particles of formate salts including lithium formate contaminated with trace amounts of transition metal formate salts.

11. The method of claim 10 further comprising sintering the formate salts at between 230° C. and 450° C. to decompose the formate salts into carbonates including lithium carbonate and carbonates of the transition metals.

12. The method of claim 10 further comprising:
   sintering the formate salts over 300° C. to decompose the lithium into lithium carbonate; and
   subsequently sintering the formate salts over 400° C. to decompose transition metal formate salts into carbonates.

13. The method of claim 10 further comprising adding deionized water to the formate salts powder to dissolve the lithium carbonate, the formate salts of the transition metals remaining undissolved.

14. The method of claim 13 further comprising combining the lithium carbonate solution with acetone to precipitate substantially pure lithium carbonate.

15. The method of claim 1 wherein the acid includes formic acid.

16. The method of claim 1 wherein the transition metals from the charge materials include Ni, Mn and Co.

17. The method of claim 2 wherein the acid is 98% formic acid and the precipitation agent is 99.5% acetone.

18. A method for recycling pure lithium from a recycling stream of batteries, comprising:
   forming a leach solution of charge material an acid, the charge material including lithium and transition metals including Ni, Mn and Co;
   heating the leach solution to around 60° C. to dissolve the lithium and forming dissolution-resistant formate salts on a particle surface of the transition metals;
   distilling the leach solution to generate a powder of lithium formate and trace quantities of transition metal formate salts;
   sintering the generated powder in atmospheric conditions to form lithium carbonate and Ni, Mn and Co carbonates;
   adding deionized water to the sintered powder to dissolve the lithium carbonate, the Ni, Mn and Co carbonates remaining in solid form;

adding the lithium carbonate solution to acetone to form a flocculant precipitation; and extracting the precipitated lithium carbonate defining at least 99% purity of the lithium.

19. The method of claim 18 wherein the acid is formic acid.

20. The method of claim 18 wherein the recycling efficiency of the lithium carbonate is at least 99.8% of the lithium in the charge material and a purity of the lithium carbonate is at least 99.9%.

* * * * *